(12) United States Patent
Mellier

(10) Patent No.: US 10,201,412 B2
(45) Date of Patent: *Feb. 12, 2019

(54) SYSTEMS AND METHODS FOR TREATING A PELVIC DISORDER

(71) Applicant: Astora Women's Health, LLC, Eden Prairie, MN (US)

(72) Inventor: Georges Mellier, Lyons (FR)

(73) Assignee: Astora Women's Health, LLC, Eden Prairie, MN (US)

( * ) Notice: Subject to any disclaimer, the term of this patent is extended or adjusted under 35 U.S.C. 154(b) by 29 days.

This patent is subject to a terminal disclaimer.

(21) Appl. No.: 15/099,912

(22) Filed: Apr. 15, 2016

(65) Prior Publication Data

US 2016/0228230 A1    Aug. 11, 2016

Related U.S. Application Data

(63) Continuation of application No. 14/306,135, filed on Jun. 16, 2014, now Pat. No. 9,339,366, which is a continuation of application No. 13/235,694, filed on Sep. 19, 2011, now Pat. No. 8,753,260, which is a continuation of application No. 12/021,092, filed on Jan. 28, 2008, now Pat. No. 8,038,594, which is a continuation of application No. 10/804,718, filed on Mar. 19, 2004, now Pat. No. 7,347,812.

(60) Provisional application No. 60/545,987, filed on Feb. 19, 2004, provisional application No. 60/504,755, filed on Sep. 22, 2003.

(51) Int. Cl.
*A61F 2/00* (2006.01)
*A61B 17/04* (2006.01)
*A61B 17/06* (2006.01)
*A61B 17/00* (2006.01)

(52) U.S. Cl.
CPC ........ *A61F 2/0063* (2013.01); *A61B 17/0469* (2013.01); *A61B 17/06* (2013.01); *A61B 17/06004* (2013.01); *A61B 17/06066* (2013.01); *A61B 17/06109* (2013.01); *A61F 2/0045* (2013.01); *A61B 2017/00805* (2013.01); *A61B 2017/06009* (2013.01); *A61B 2017/06076* (2013.01); *A61F 2002/0072* (2013.01)

(58) Field of Classification Search
CPC ................ A61B 17/0469; A61B 17/06; A61B 17/06066; A61B 17/06109; A61B 2017/00805; A61B 2017/06009; A61B 2017/06076; A61F 2/0045; A61F 2/0063; A61F 2002/0072
USPC .............................. 600/29–32; 128/897, 898
See application file for complete search history.

(56) References Cited

U.S. PATENT DOCUMENTS 6,306,079 B1 *  10/2001  Trabucco ............... A61F 2/0045
                                                          600/30
7,347,812 B2 *   3/2008  Mellier .............. A61B 17/0469
                                                          600/29

(Continued)

*Primary Examiner* — Samuel Gilbert
(74) *Attorney, Agent, or Firm* — Skaar Ulbrich Macari, P.A.

(57) ABSTRACT

Surgical instruments for pevlic repair are disclosed. The surgical instruments have straight portions and helical portions. Surgical methods for treating prolapse and other pelvic disorders are also disclosed, including passing a distal end region of the surgical instruments through pelvic tissue, associating an implant with the surgical instruments, and securing the implant in place to stabilize the vagina.

17 Claims, 19 Drawing Sheets

(56) References Cited

U.S. PATENT DOCUMENTS

| | | | |
|---|---|---|---|
| 8,753,260 B2 * | 6/2014 | Mellier | A61B 17/0469 600/30 |
| 9,339,366 B2 * | 5/2016 | Mellier | A61B 17/0469 |
| 2002/0165566 A1 * | 11/2002 | Ulmsten | A61B 17/04 606/151 |
| 2002/0188169 A1 * | 12/2002 | Kammerer | A61B 1/00087 600/30 |

* cited by examiner

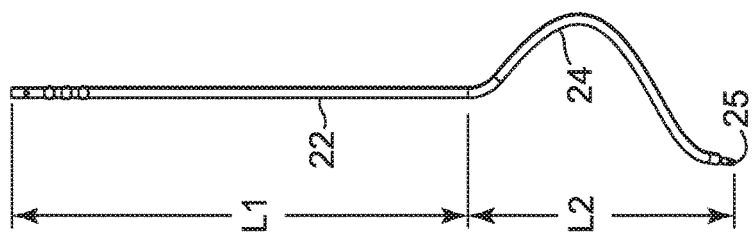
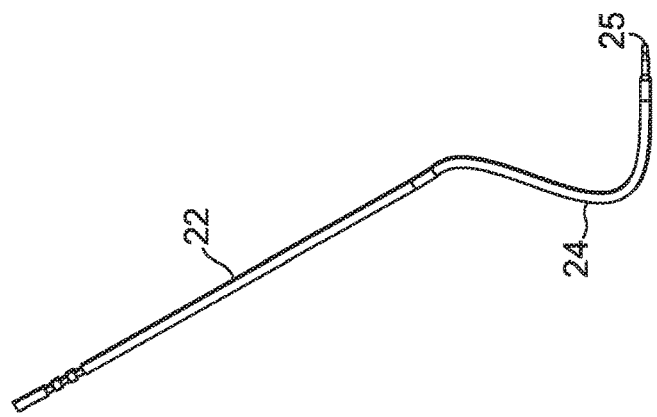
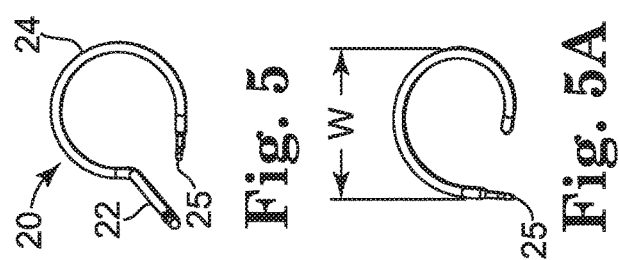
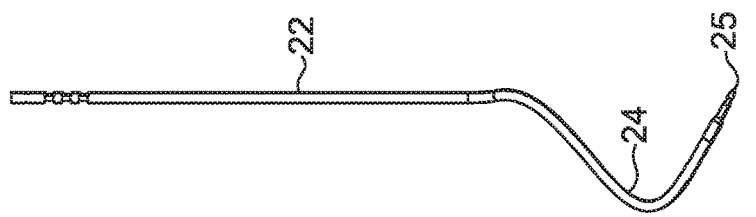
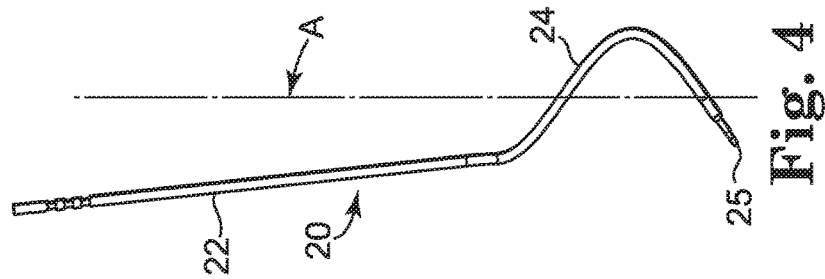

US 10,201,412 B2

SYSTEMS AND METHODS FOR TREATING A PELVIC DISORDER

CROSS-REFERENCE TO RELATED APPLICATIONS

This present application is a Continuation of U.S. patent application Ser. No. 14/306,135, filed on Jun. 16, 2014, which is a Continuation of U.S. patent application Ser. No. 13/235,694, filed on Sep. 19, 2011 and Issued as U.S. Pat. No. 8,753,260 on Jun. 17, 2014, which is a Continuation of U.S. patent application Ser. No. 12/021,092, filed on Jan. 28, 2008 and Issued as U.S. Pat. No. 8,038,594 on Oct. 18, 2011, which is a Continuation of U.S. patent application Ser. No. 10/804,718, filed on Mar. 19, 2004 and Issued as U.S. Pat. No. 7,347,812 on Mar. 25, 2008, which claims priority to and the benefit of U.S. Provisional Patent Application Nos. 60/545,987, filed Feb. 19, 2004 and 60/504,755, filed Sep. 22, 2003; with the entire contents of each referenced application fully incorporated herein by reference.

FIELD OF THE INVENTION

The present invention relates generally to treating a pelvic disorder in a patient and, more specifically, to systems and methods of using surgical implants, tools, and techniques to treat vaginal prolapse and other pelvic disorders.

BACKGROUND OF THE INVENTION

There are a wide variety of surgical techniques used to repair vaginal prolapse and apical defects. There is no consensus supporting the efficacy of one technique over the others.

Surgical approaches vary. They include vaginal, abdominal and laparoscopic surgical approaches. See Richter K: *Massive Eversion of the Vagina: Pathogenesis, Diagnosis and Therapy of the True Prolapse of the Vaginal Stump*, Clin. Obstet Gynecol 25:897-912 (1982); Diana et al., *Treatment of Vaginal Vault Prolapse with Abdominal Sacral Colpopexy Using Prolene Mesh*, American Journal of Surgery, Vol. 179, (February 2000), Pps. 126-128; Winters et al., *Abdominal Sacral Colpopexy and Abdominal Enterocele Repair in the Management of Vaginal Vault Prolapse*, Urology 56 (Suppl 6A) (2000): 55-63; and Paraiso et al, *Laparoscopic Surgery for Enterocele, Vaginal Apex Prolapse and Rectocele*, Int Urogynecol J (1999), 10:223-229.

Abdominal sacral colpopexy is considered to be an especially efficacious treatment, but it has been criticized for its inability to address posterior wall defects or perineal descent problems. This can result in persistent or altered defactory issues. See Bassler et al., *Abdominal Sacrocolpopexy and Anatomy and Function of the Posterior Compartment*, Obstet. Gyn 2001; 97:678-683. These procedures are generally considered invasive.

Sacrospinous ligament suspensions are also popular. However, these procedures have been criticized for distorting support symmetry about the vaginal axis. This could contribute to a predisposition for future defects in the anterior compartment. See Paraiso et al., *Pelvic support defects and visceral and sexual function in women treated with sacrospinous ligament suspension and pelvic reconstruction*. Am J Obstet Gyn 1996; 175:1423-1431. See also, Guner et al., *Transvaginal Sacrospinous Colpopexy for Marked Uterovaginal and Vault Prolapse*, Inter. J. of Gynec. & Obstetrics, 74 (2001) Pps. 165-170. This fixation is believed to risk complications through damage to the pudendal neurovascular bundle and sciatic nerve. Uterosacral ligament suspension is another repair procedure, but risk of ureteral injury still exists.

PCT Publication No. WO 00/64370 (Gaston) describes a device for treating a prolapse by vaginal suspension. The device comprises an elongate, flexible, pierced material, a suture connected to the material and a suture needle joined to the suture. The device is long enough to enable posterior suspension of the vagina at the promontory (i.e. the front upper part of the sacrum). The other end of the device includes a distal portion having a width such that it can cover at least a large part of the posterior part of the vagina, a rounded cut-out with dimensions that enable it to be engaged around the base of the vagina on at least a large part of the lower half of the wall of the vagina. The suture is connected to the article so that it is offset sidewise in relation to the cut-out.

PCT Publication No. WO 00/27304 (ORY et al.) discloses a suspension device for treating prolapse and urinary incontinence. The device comprises at least one filiform suspension cord with limited elasticity and at least two anchoring parts linked to the ends of the cord.

PCT Publication No. WO 02/078552-A1 discloses an apparatus for treating vaginal vault disorders.

Published U.S. Pat. Appl. Nos. 2003/0220538-A1 and 2003/0176762 purport to disclose surgical instruments for treating prolapse.

U.S. Pat. No. 5,112,344 and PCT Publication No. PCT/US02/32284 disclose surgical devices for female pelvic health procedures. The IVS Tunneller device is available from U.S. Surgical of Norwalk, Conn. The IVS device comprises a fixed delta wing handle, a hollow metal tube and a stylet that is placeable within the tube. The stylet has a rounded plastic tip on one end and an eyelet at the other end. The device may be used to implant a polypropylene tape for infracoccygeal sacropexy and other surgical procedures. See Farnsworth, *Posterior Intravaginal Slingplasty (Infracoccygeal Sacropexy) For Severe Posthysterectomy Vaginal Vault Prolapse—A Preliminary Report on Safety and Efficacy*, Int. Urogynecol. J. (2002) 13:4-8; Petros, *Vault Prolapse II: Restoration of Dynamic Vaginal Supports by Infracoccygeal Sacropexy, an Axial Day-Case Vaginal Procedure*, Int Urogynecol J (2001) 12:296-303; and Petros, *The Intravaginal Slingplasty Operation, a Minimally Invasive Technique for Cure of Urinary Incontinence in the Female*, Aust. NZ J Obstet Gynaecol, (1996); 36: 4:453.

A single, rigid, hollow metal tube is associated with the IVS Tunneller device. This single tube passes through two separate regions of the patient's body with the attendant risk of cross contamination. The outer diameter of the tube is also relatively large (about 0.25 inches) with the attendant risk of tissue damage due to a large diameter needle.

The polypropylene tape supplied with the IVS Tunneller is a thin, rectangular shape, believed to be approximately 8 mm×350 mm. The thin, rectangular tape supplied with the IVS Tunneller is not believed to be extensible. Under a longitudinal force, the implant is highly resistant to elongation. It is believed that inextensible polypropylene tapes may be apt to exhibit a greater association with erosion and failure.

A recent abstract describes using a 15×14 cm implant, placed transvaginally, to repair the anterior, median perineal defect. See Mouly et al., *Vaginal Reconstruction of a Complete Vaginal Prolapse: The Trans Obturator Repair*, Journal of Urology, April 2003, Vol 169 (4) supplement, p 183, Abstract # V 702, AUA Apr. 26-May 1, 2003, Chicago, Ill. The abstract also discloses that wings of the mesh are inserted through the obturator holes. Another publication describes an anterior wall repair. See Salomon et al., *Treatment of Anterior Vaginal Wall Prolapse with Porcine Skin Collagen Implant by the Transobturator Route: Preliminary Results*; European Urology 45 (2004), 219-245. This procedure utilizes an Emmet needle to pierce the obturator foramen.

SUMMARY OF THE INVENTION

The present invention is directed to novel surgical instruments for surgical procedures that treat prolapse. Novel surgical procedures that utilize such instruments are also disclosed.

In one aspect, the present invention comprises a surgical instrument for inserting an implant for treating female prolapse. The surgical instrument comprises a handle and a needle portion. The needle portion has a straight portion emerging from the handle and a generally helical portion having a distal end region. The needle portion is sized and shaped so that the distal end region may initially be moved through a patient's obturator foramen toward the region of the patient's ischial spine, and then toward a vaginal incision in the region of the vaginal apex, so that an implant may be received by the distal end of the needle and moved from the vaginal incision through the patient's obturator foramen.

The helical portion may comprise either a left or a right handed helical portion. Preferably, the needle portion has a generally circular cross section with a diameter of less than about 5.5 mm and more than about 0.5 mm. In a preferred embodiment, the straight portion of the instrument has a longitudinal axis and the helical portion has a length, measured along the longitudinal axis of the straight portion, of more than 2 inches and less than twelve inches. In the preferred embodiment, the helical portion has a width of more than about 1 inch and less than about 9 inches. Preferably, the helical portion has a pitch of at least 2 inches and less than seven inches and a radius of at least 0.5 inches and less than four inches.

In a preferred embodiment, the straight portion of the instrument has a longitudinal axis and the helical portion has an axis that is not parallel to the axis of the straight portion. The axis of the straight portion and the axis of the helical portion form an angle, preferably of about 8 degrees. The distal end portion of the instrument points away from the handle and at an acute angle relative to a plane that is perpendicular to the longitudinal axis of the straight portion of the instrument.

In another aspect, the present invention comprises an assembly of surgical instruments for treating female prolapse. The assembly comprises a first surgical instrument comprising a handle; a needle portion having a straight portion emerging from the handle and a generally right handed helical portion having a distal end region. The needle portion is sized and shaped so that the distal end region may initially be moved through a patient's obturator foramen toward the region of the patient's ischial spine, and then toward a vaginal incision in the region of the vaginal apex. The assembly includes a second surgical instrument comprising a handle; a needle portion having a straight portion emerging from the handle and a generally left handed helical portion having a distal end region. The needle portion of the second needle is sized and shaped so that the distal end region may initially be moved through a patient's obturator foramen toward the region of the patient's ischial spine, and then toward a vaginal incision in the region of the vaginal apex. The assembly also includes an implant for treating the prolapse.

In a preferred embodiment, the assembly may include a pair of dilating connectors and insertion sleeves surrounding the implant. Alternatively, the distal end portions of the needles may include eyelets. The implant may be extensible or inextensible. Preferably, an insertion sleeve accompanies an extensible implant.

A surgical procedure is also described. The surgical procedure can include the steps of: i) providing a first surgical instrument comprising a handle, a needle portion having a straight portion emerging from the handle and a generally right handed helical portion having a distal end region; a second surgical instrument comprising a handle, a needle portion having a straight portion emerging from the handle and a generally left handed helical portion having a distal end region; ii) creating a vaginal incision; iii) incising the patient's skin in the region of the patient's obturator foramen on a first side of the patient, iv) passing the distal end portion of the first surgical instrument through the obturator foramen and then through the vaginal incision; v) associating the implant with the first surgical instrument; vi) incising the patient's skin in the region of the patient's obturator foramen on a second side of the patient, vii) passing the distal end portion of the second surgical instrument through the obturator foramen and then through the vaginal incision; viii) associating the implant with the second surgical instrument; ix) moving the distal end portion of the first surgical instrument from the vaginal incision through the patient's obturator foramen with an end of the implant associated with the distal end portion; x) moving the distal end portion of the second surgical instrument from the vaginal incision through the patient's obturator foramen with an end of the implant associated with the distal end portion; and xi) attaching the implant to the vagina. Preferably, the step of creating a vaginal incision includes the step of creating a vaginal incision in a region of the apex of the vagina. Also preferably, the step of passing the distal end portion of the first surgical instrument through the obturator foramen and then through the vaginal incision includes the step of passing the distal end of the instrument through the inferior part of the obturator membrane in the region of the obturator foramen above the ischio-pubic ramus.

BRIEF DESCRIPTION OF THE DRAWINGS

Other features and advantages of the present invention will be seen as the following description of particular embodiments progresses in conjunction with the drawings, in which:

FIG. 4 is a top view of a surgical instrument showing an axis for a helical portion of the instrument;

FIG. 4A is another view of the surgical instrument of FIG. 4;

FIG. 5 is an end view of the surgical instrument of FIG. 4, taken in a plane substantially perpendicular to the axis of the helical portion of the instrument;

FIG. 5A is a view of the instrument of FIG. 4 taken in a plane substantially perpendicular to the axis of a straight portion of the instrument;

FIG. 6 is another view of the instrument of FIG. 4;

FIG. 6A is another view of the instrument of FIG. 4;

FIGS. 9 through 22 schematically illustrate the use of the assembly of surgical articles of FIG. 8 in treating prolapse, wherein:

FIG. 9 shows a surgical instrument just as it begins to traverse the patient's right obturator foramen;

FIG. 10 illustrates the distal end portion of a surgical instrument after it has traversed the obturator foramen and while it is being moved in the general direction of the ischial spine;

FIG. 11 illustrates the distal end portion of the surgical instrument as it is being moved toward a vaginal incision and a surgeon's finger;

FIG. 12 illustrates the surgical needle after the distal end region has entered the vaginal vault;

FIG. 13 illustrates a connecting dilator and a portion of an implant assembly as the connecting dilator is being moved toward the distal end region of the surgical instrument;

FIG. 14 illustrates the connecting dilator after it has been connected to the distal end region of the surgical instrument;

FIG. 15 illustrates the implant assembly after one end portion has been guided by the surgical instrument through a vaginal incision, through tissue and then toward an incision adjacent the obturator foramen;

FIG. 16 illustrates the end portion of the implant assembly after it has traversed the obturator foramen and emerged from a skin incision;

FIG. 17 illustrates a scissors after it has separated the surgical instrument and dilating connector from the remaining portion of the implant assembly;

FIG. 18 illustrates a second surgical instrument after it has passed through the patient's left obturator foramen, and after the distal end region of the surgical instrument has emerged through a vaginal incision, which figure also illustrates a second dilating connector attached to the distal end region of the second needle;

FIG. 19 illustrates the implant assembly after the surgical instrument has guided the dilating connector through the patient's left obturator foramen;

FIG. 20 illustrates a surgical scissors being used to separate the dilating connector (with attached surgical instrument) from the rest of the implant assembly;

FIG. 21 illustrates insertion sheaths of the implant assembly being removed from the body; and FIG. 22 illustrates the implant that corrects the vaginal prolapse just prior to it being trimmed to the skin incisions adjacent the patient's obturator foramen.

DETAILED DESCRIPTION OF THE INVENTION

Figure 3A:
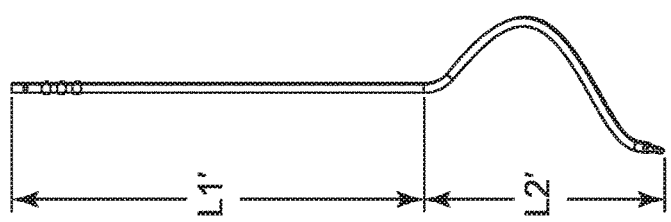
FIG. 3A is another view of the instrument of FIG. 1.
Figure 3:
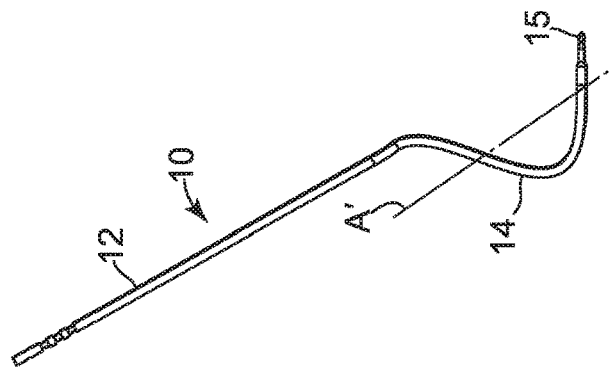
FIG. 3 is another view of the instrument of FIG. 1.
Figures 2, 2A:
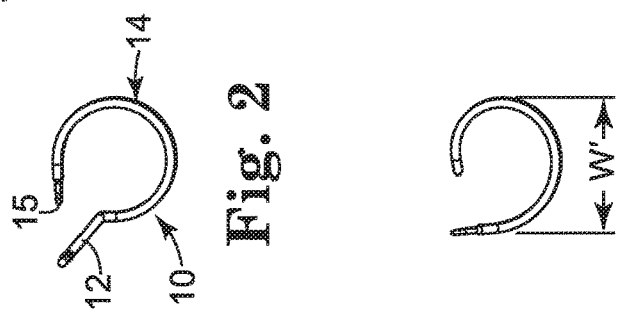
FIG. 2 is an end view of the surgical instrument of FIG. 1, taken in a plane substantially perpendicular to the axis of the helical portion of the instrument.
FIG. 2A is a view of the instrument of FIG. 1 taken in a plane substantially perpendicular to the axis of a straight portion of the instrument.
Figure 1A:
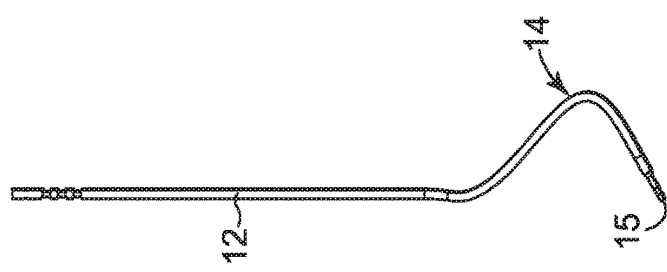
FIG. 1A is another view of the surgical instrument of FIG. 1.
Figure 1:
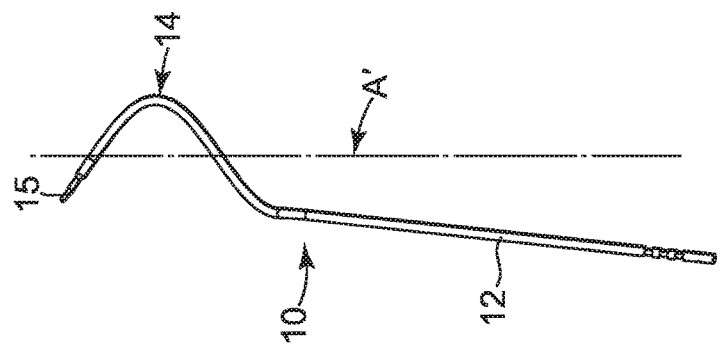
FIG. 1 is a top view of a surgical instrument showing an axis for a helical portion of the instrument.

The following description is meant to be illustrative only and not limiting. Other embodiments of this invention will be apparent to those of ordinary skill in the art in view of this description.

FIGS. 1-3A illustrate a surgical instrument for use on one side of the patient's body. FIGS. 4-6A disclose a surgical instrument for use on the opposite side of the patient's body.

The surgical instrument 10 includes a straight portion 12, a helical portion 14, and a distal end region 15. Similarly, the surgical instrument 20 includes a straight portion 22, a helical portion 24, and a distal end region 25. Preferably, the surgical instruments 10 and 20 include handles 11 and 21 (FIG. 8) which are not shown in FIGS. 1-6A.

The surgical instruments 10 and 20 are adapted for a surgical procedure for reconstruction of the vaginal vault, as described more fully below. The cross sectional shape of the straight and helical portions can be of a wide variety of shapes and is preferably small. For a circular cross section, the diameter is preferably less than about 5.5 mm and more than about 0.5 mm.

As an example, not intended to be limiting, the surgical instrument 10 may have a diameter of 0.125 inches. The length L1' is preferably more than about 5 inches and may be about 6 inches, the length L2' is preferably more than 1 inch, more preferably more than 2 inches and even more preferably about 2.76 inches. The length L1' is preferably less than twelve (12) inches. The width W' is preferably more than one inch and less than about 9 inches. In a preferred embodiment the width W' may be about 2.15 inches. Preferably about two inches of the straight portion 12 project from the end of the handle 11. The helical portion 14 preferably has a radius of at least 0.5 inches, more preferably 0.825 inches and a pitch of at least about 2 inches preferably about 3.65 inches. The surgical instrument may be formed about a mandrel with a diameter of 1.5 inches and a groove (for receiving the surgical instrument) with a pitch of 3 inches. Notably, the axis A' of the helical portion 14 is offset from the longitudinal axis of the straight portion 12 (see FIGS. 1 and 3). In this embodiment, the offset is about 8 degrees. In a preferred embodiment, the offset for both instruments 10 and 20 is the same and at least 5 degrees. The bend between the straight and helical portions 12 and 14 may have a radius of about 0.3 inches.

Preferably, the distal end portion 15 of the surgical instrument points away from the handle 11 (FIG. 8) and at an acute angle relative to a plane that is perpendicular to the longitudinal axis of the straight portion 12 of the instrument.

Similarly, for instrument 20, length L1 may be about 6 inches, the length L2 is about 2.76 inches, and width W of about 2.15 inches. Preferably about two inches of the straight portion 22 project from the end of the handle 21. Again, the axis A of the helical portion 24 is offset from the longitudinal axis of the straight portion 22. The helical portion 24 preferably has a radius of 0.825 inches and a pitch of about 3.65 inches. The ranges for the size and shape of the instrument 20 are the same as described above for the instrument 10.

One of the helical portions 14 and 24 has a right hand helix and the other has a left hand helix. The surgical instruments 10 and 20 may be constructed from any suitable polymeric or metallic material. One suitable material is stainless steel 17-4 PH hardened to H900.

Figure 8:
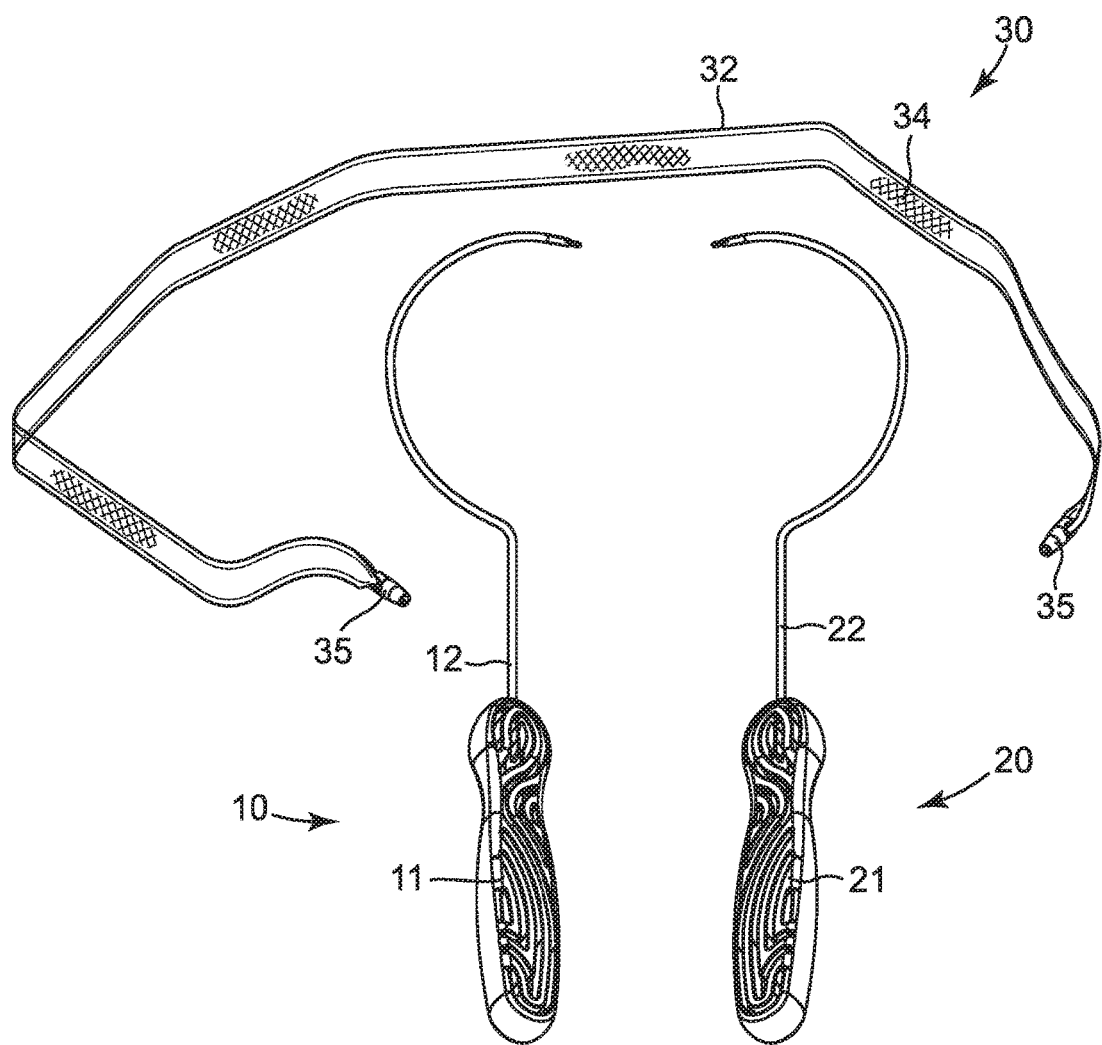
FIG. 8 is a perspective view of an assembly of surgical articles for use in a subsequent procedure for treating prolapse.

FIG. 8 shows an assembly of surgical articles 10, 20 and 30 for treating prolapse. The assembly preferably includes surgical articles 10 and 20 and an implant assembly 30 with dilating connectors 35, implant 34 and separable insertion sheath 32. The dilators and insertions sheath are optional. Alternatively, for example, the distal end portions of the surgical instruments 10 and 20 may include eyelets for receiving the implant 34.

The distal end regions 15 and 25 may have surfaces that are specially shaped to engage complementary surfaces on the dilating connectors 35 of an implant assembly 30. Such assemblies are disclosed in published U.S. Pat. Application Nos. 2003/0171644-A1 and 2003/0176875-A1.

The implant assemblies 30 typically include an implantable material 34 that remains in the body. The implantable material may comprise synthetic or non-synthetic materials or hybrids, composites or combinations thereof.

A synthetic material is preferable. Suitably synthetic materials include polymerics, and plastics and any combination of such materials. Commercial examples of such materials include Mersile™, Teflon™, Gore-Tex™, Silastic™, Marlex™, Prolene™, and Vaskutek™. Other examples of suitable materials include those disclosed in U.S. Pat. No. 6,652,450. Specific examples of synthetic sling materials include absorbable and non-absorbable materials such as polypropylene, polyethylene, nylon, PLLA and PGA. Additional meshes are disclosed in Dietz et al., *Mechanical Properties of Urogynecologic Implant Materials*, Int. Urogynecol. J. (2003) 14: 239-243; and Iglesia et al., *The Use of Mesh in Gynecologic Surgery*, Int. Urogynecol. J. (1997) 8:105-115.

Possible non-synthetic materials include allografts, homografts, heterografts, autologous tissues, cadaveric fascia and fascia lata.

Surgical Methods

Figure 7:
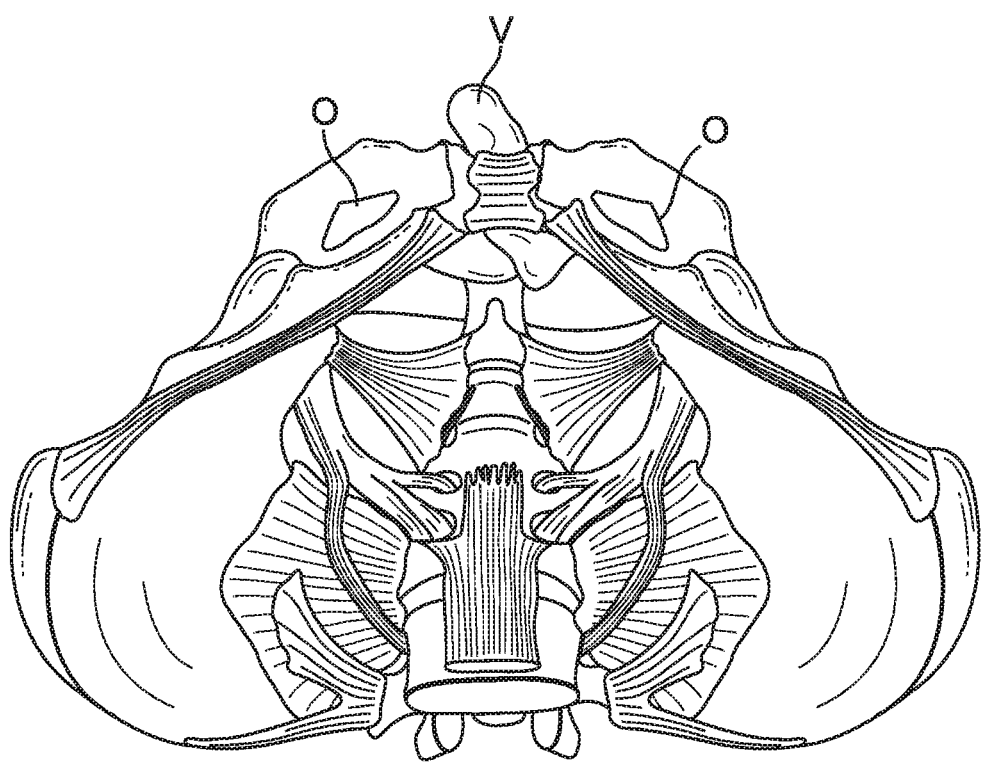
FIG. 7 is a schematic view of portions of a human female pelvic region, showing a prolapsed vagina.

In another aspect, the present invention comprises a surgical method, e.g. for prolapse repair. FIG. 7 shows a prolapsed vagina V and a female pelvis with obturator foramen O.

FIGS. 9 through 22 illustrate one example of a surgical procedure for treating prolapse. The goal of the procedure is to perform a vaginal vault suspension using an implant fixed relative to the vagina (e.g. on or near the vaginal apex). FIG. 8 shows surgical instruments 10 and 20 and implant assembly 30 that are conveniently assembled for purposes of conducting the subsequent surgery. The surgical instruments 10 and 20 and implant assembly 30 may optionally be packaged together and opened just prior to the procedure. The implant assembly 30 preferably includes an implantable surgical mesh 34, a separable insertion sleeve 32 and a pair of dilating connectors 35.

For fitting the implant 34, at least two routes are possible: one with an anterior dissection and one with posterior dissection. This procedure can be conducted after previous or concomitant hysterectomy and in cases of uterus preservation. Preferably, specific instruments 10 and 20 are passed through the membrane OM in the region of the obturator foramen O to place the implant 34. The implant 34 stabilizes the vaginal vault by fixation on both sides through, e.g, pelvic muscles and membranes.

Posterior Route Fixation

The posterior vaginal wall is incised longitudinally from the apex AP down to the perineum incision. (Lowest part incision may be done for posterior myorraphy). The rectum is dissected from the vaginal wall, preferably substantially the entire portion. The para-rectal space is opened in both sides with dissection deeply to the ischial spines IS. The index finger of the surgeon can palpate levator ani and deeper, the ischial spine IS.

Figure 9:
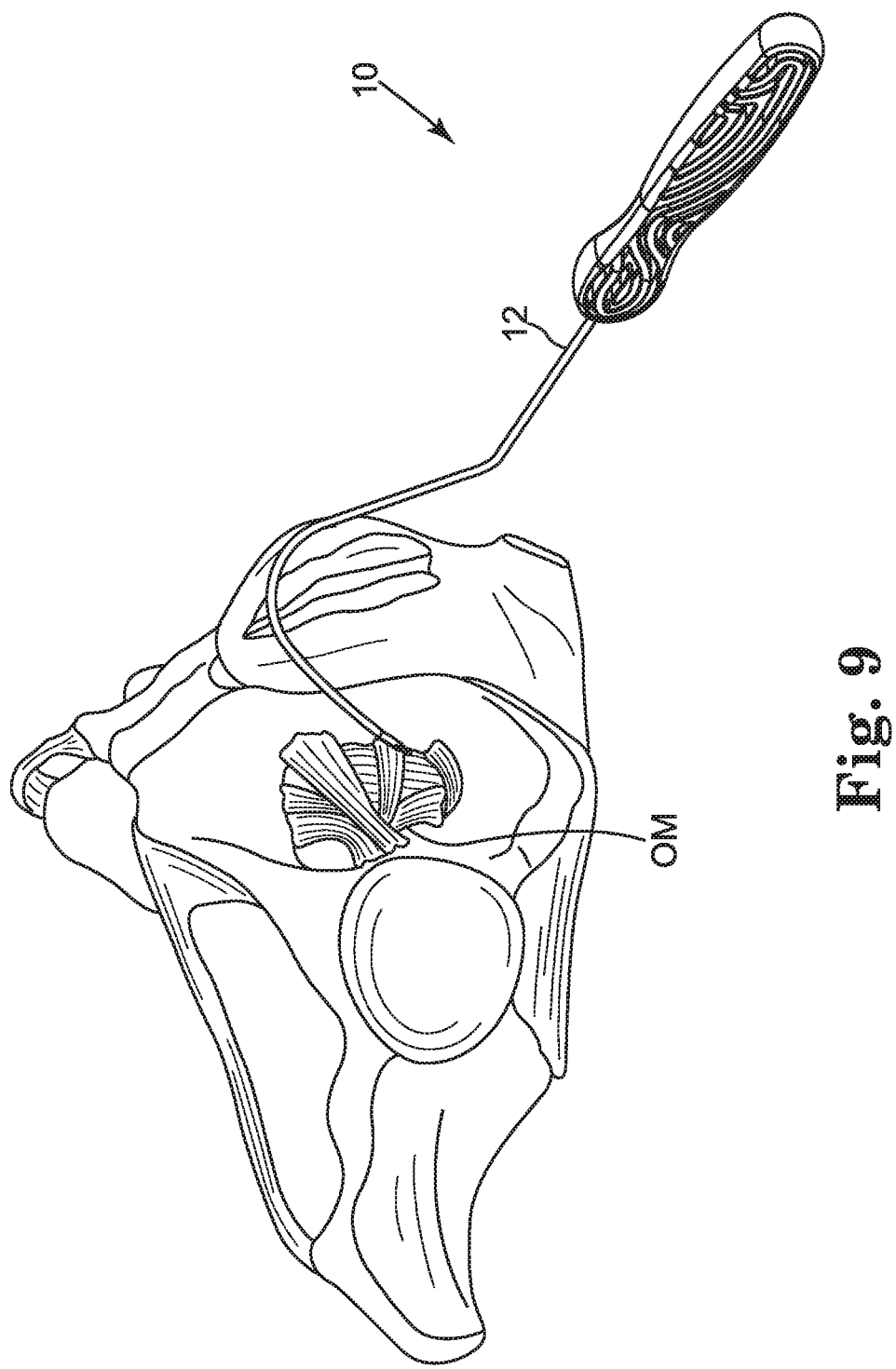
Figure 10:
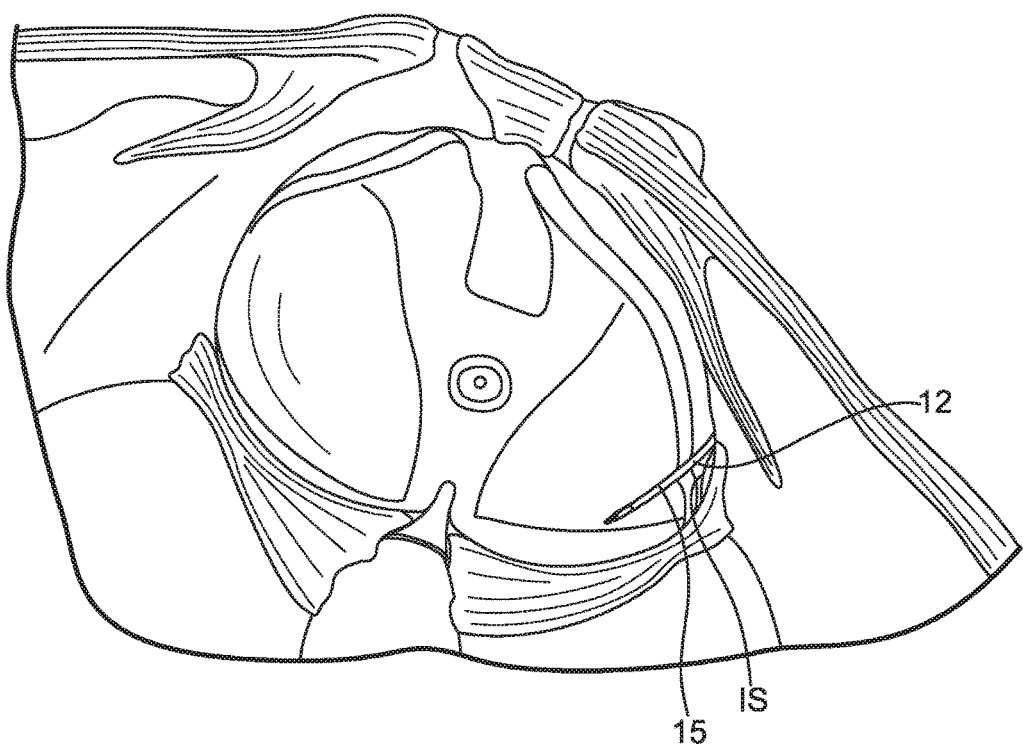
Figure 11:
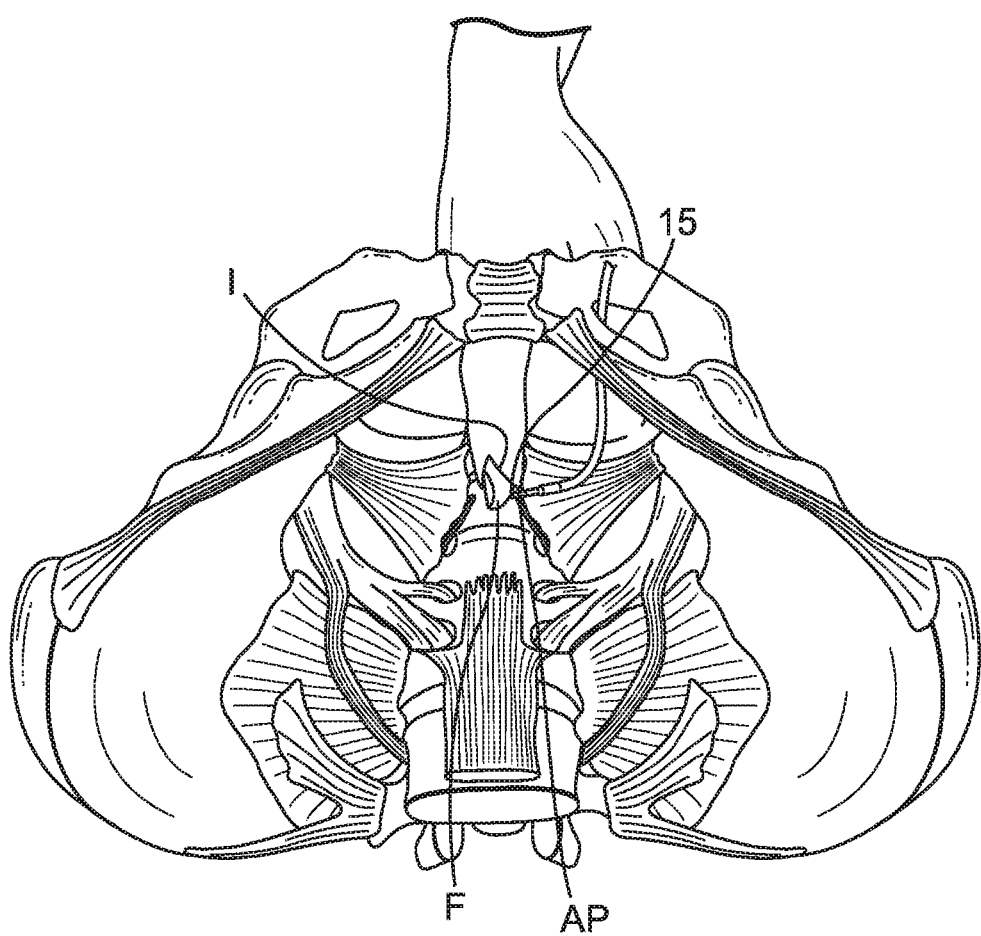
Figure 12:
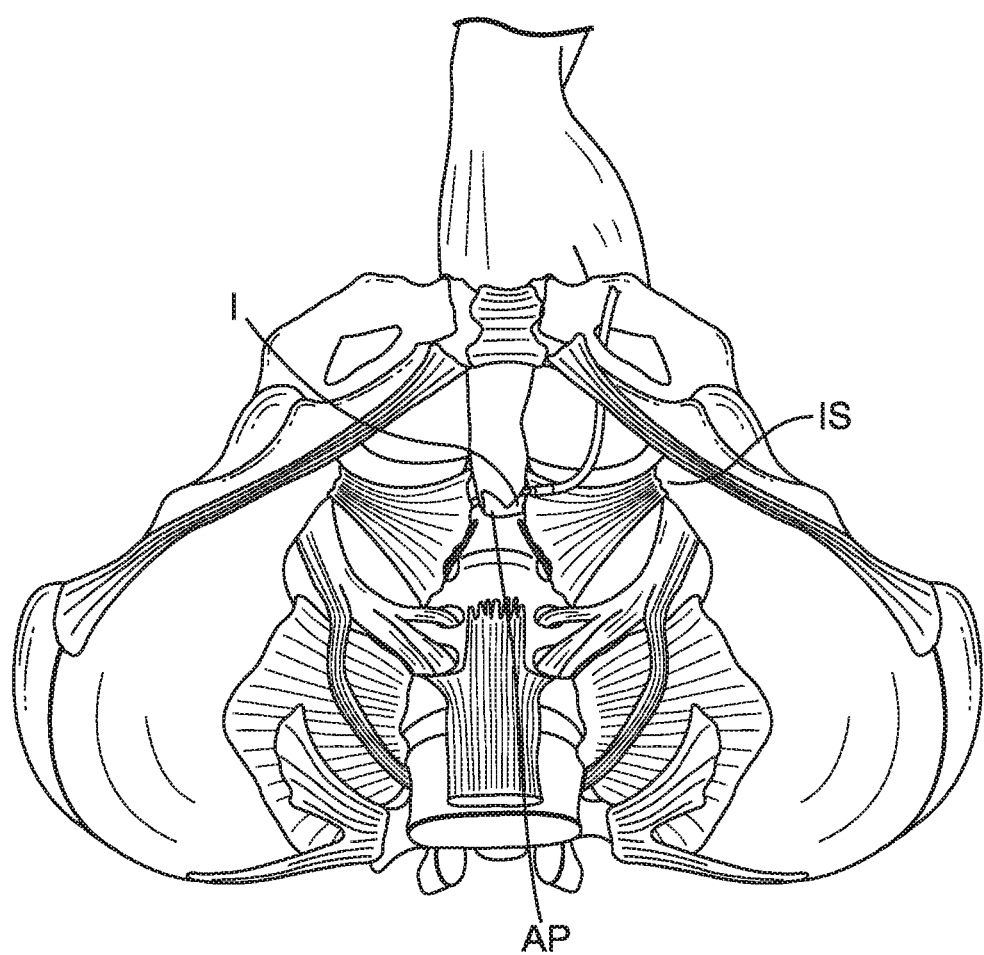

FIG. 9 schematically illustrates a preferred needle passage. The needle passage is preferably through the inferior part of the obturator membrane O in the region of the obturator foramen above the ischio-pubic ramus. After a small skin incision, the distal end portion 15 of the instrument 10 is pushed through the obturator membrane O. As shown in FIG. 10, the distal end portion 15 is moved initially toward the region of the patient's ischial spine IS. The surgeon's index finger can palpate the needle tip through the muscular wall going to the ischial spine IS. The distal end 15 of the instrument is pushing out through the levator ani when it arrives at the level of the spine. FIG. 11 shows the surgeon's finger palpating the distal end 15 of the needle. FIG. 12 shows the arrangement after the distal end portion of the needle after it has passed through a vaginal incision I.

Figure 13:
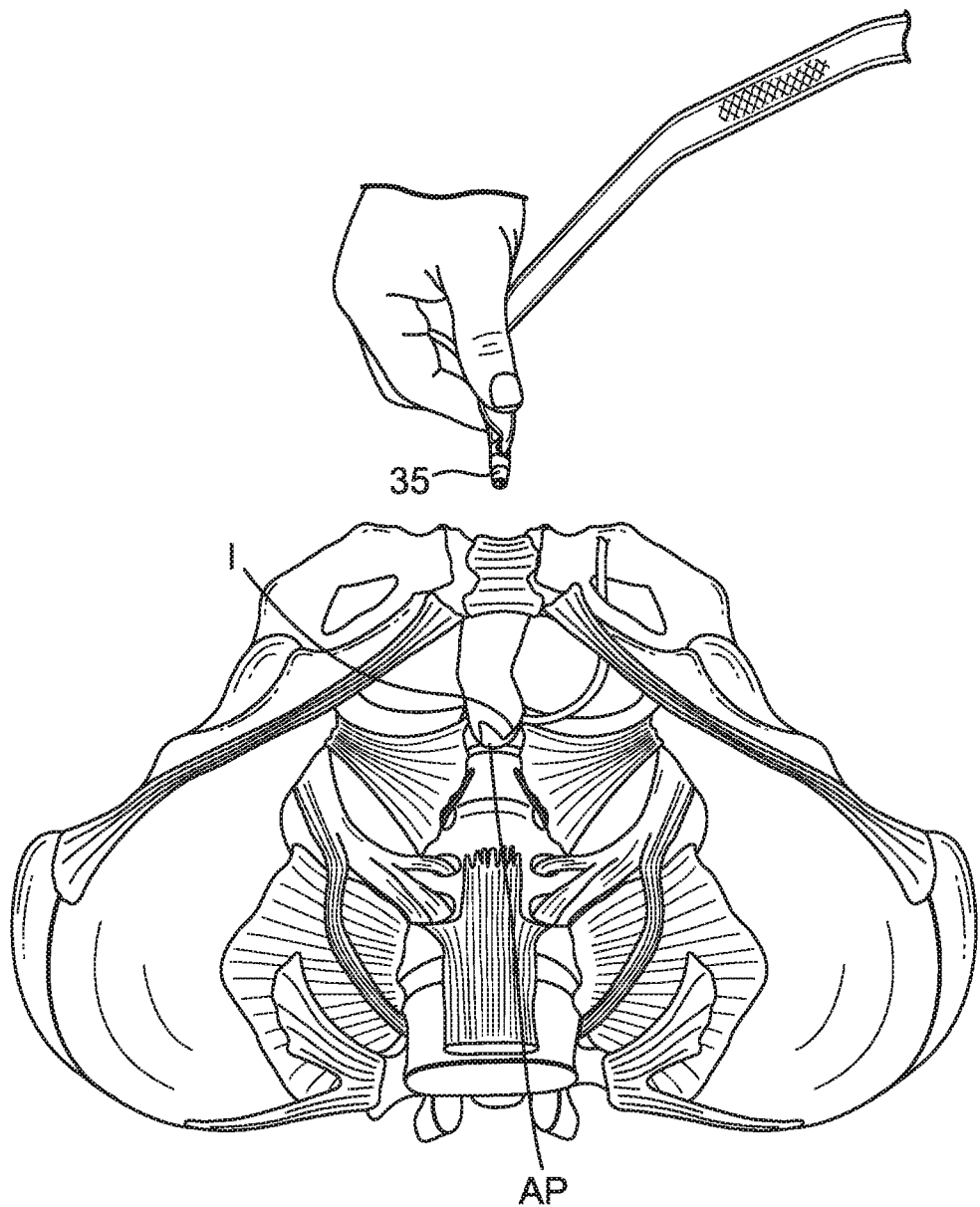
Figure 14:
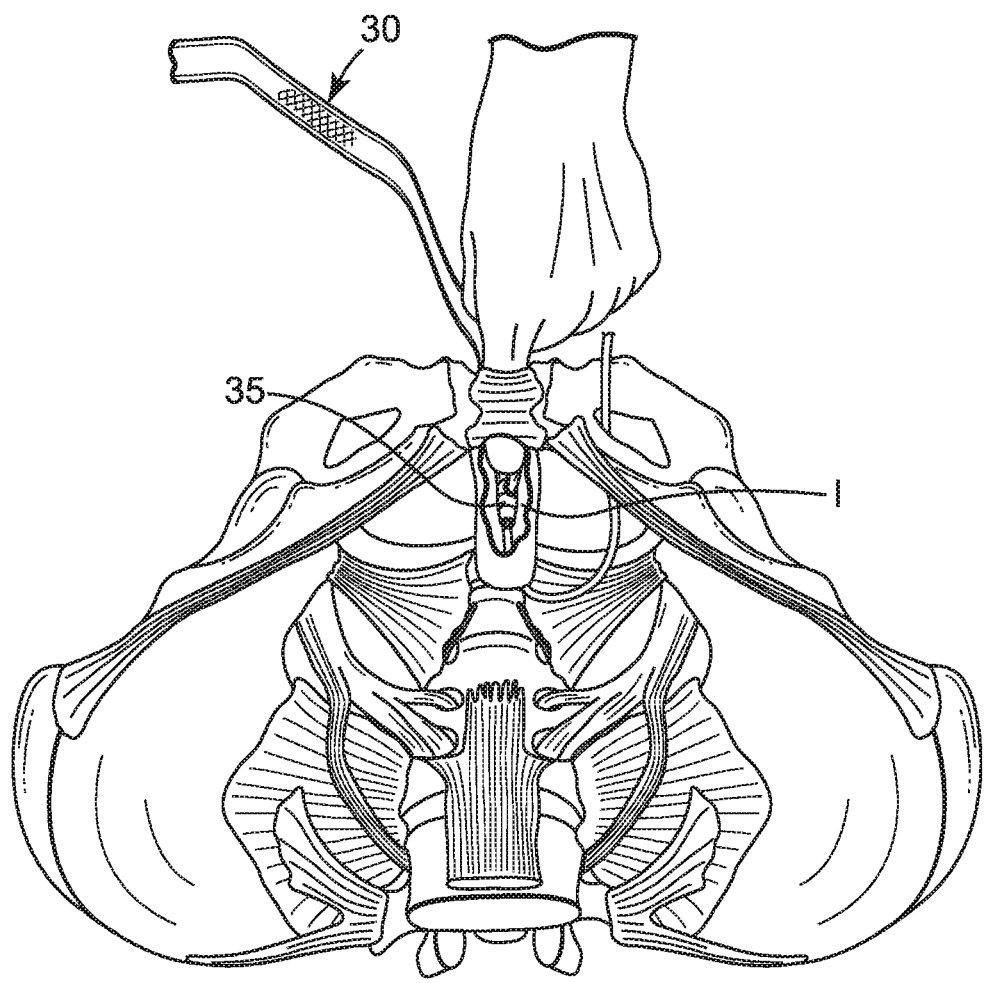
Figure 15:
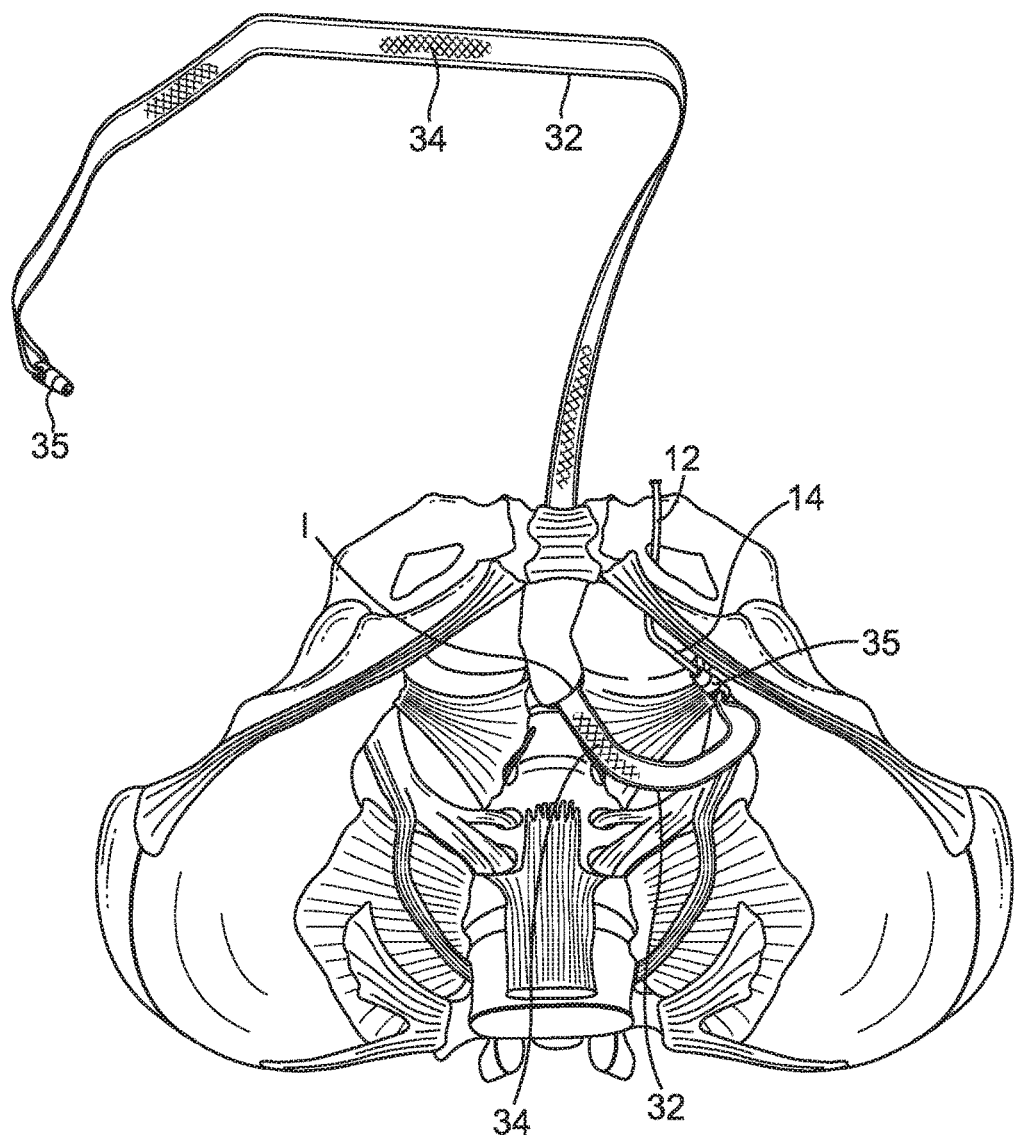
Figure 16:
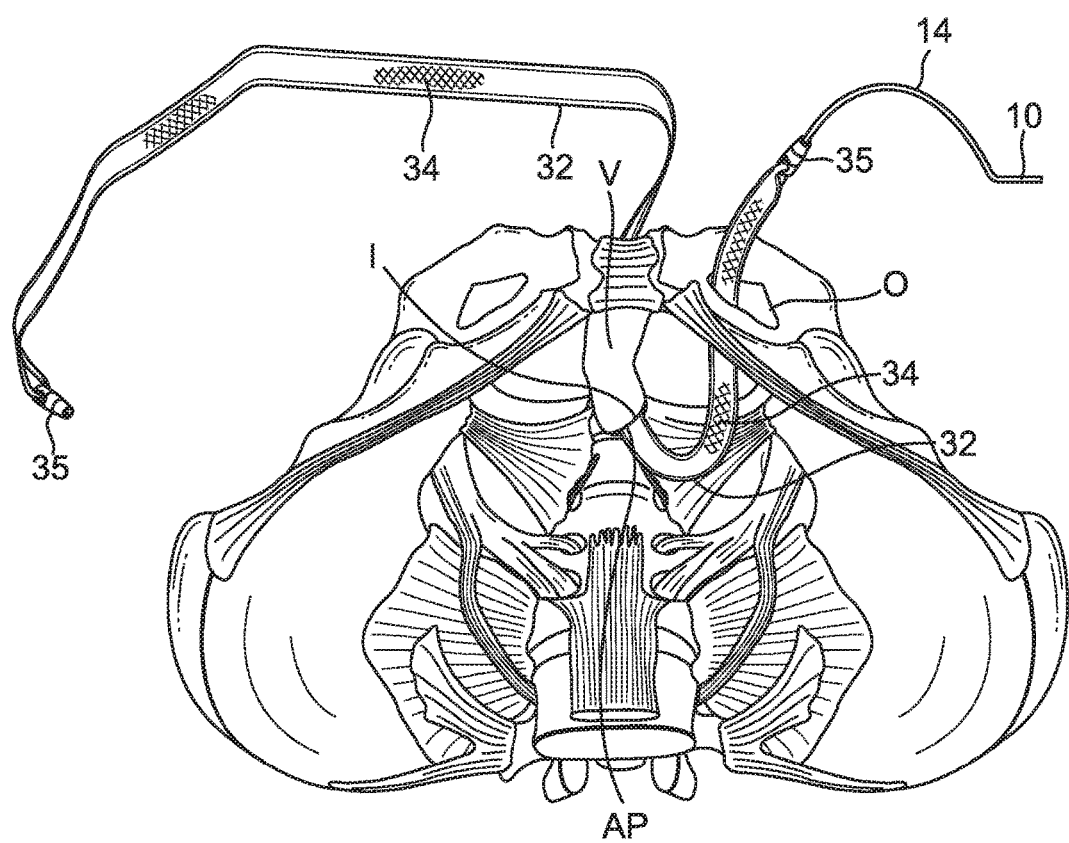
Figure 17:
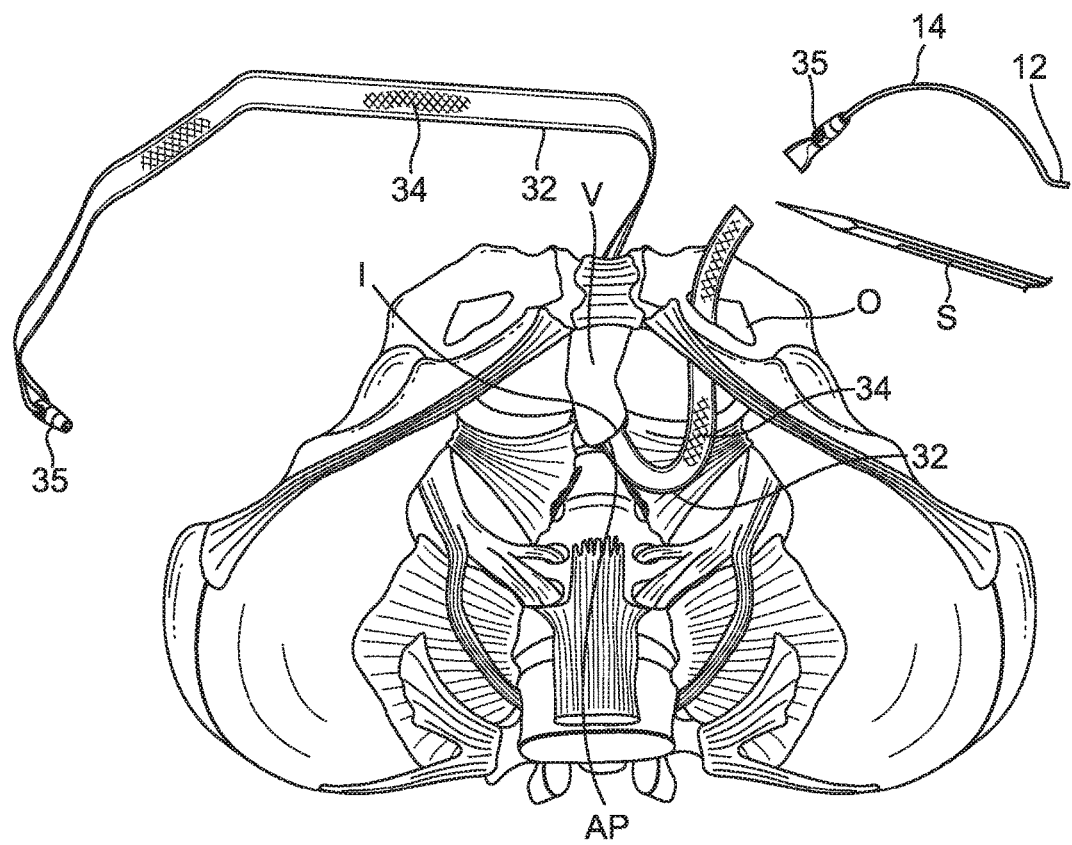

In FIG. 13, the surgeon moves the dilating connector 35 of the implant assembly 30 toward the end portion 15 of the needle. The dilating connector 35 is then connected to the needle tip (FIG. 14). This is shown taking place within the vaginal region. Preparation for this step is shown in FIG. 13. As shown in FIGS. 15 and 16, the needle 12 is pulled back out obturator O and the implant assembly 30 is essentially in place on one side of the patient. FIG. 17 illustrates a scissors S after it has separated the surgical instrument 10 and dilating connector 35 from the remaining portion of the implant assembly 30.

Figure 18:
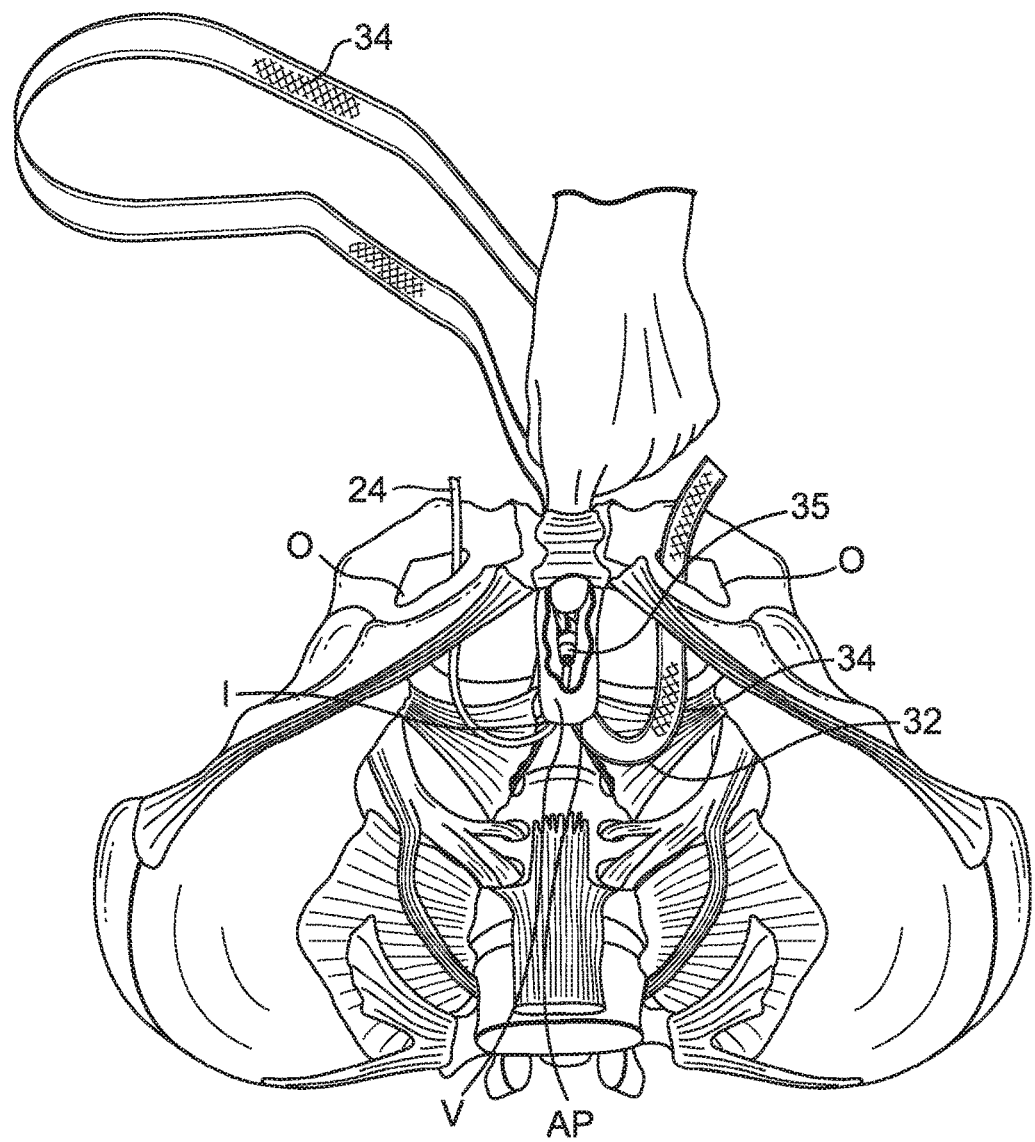
Figure 19:
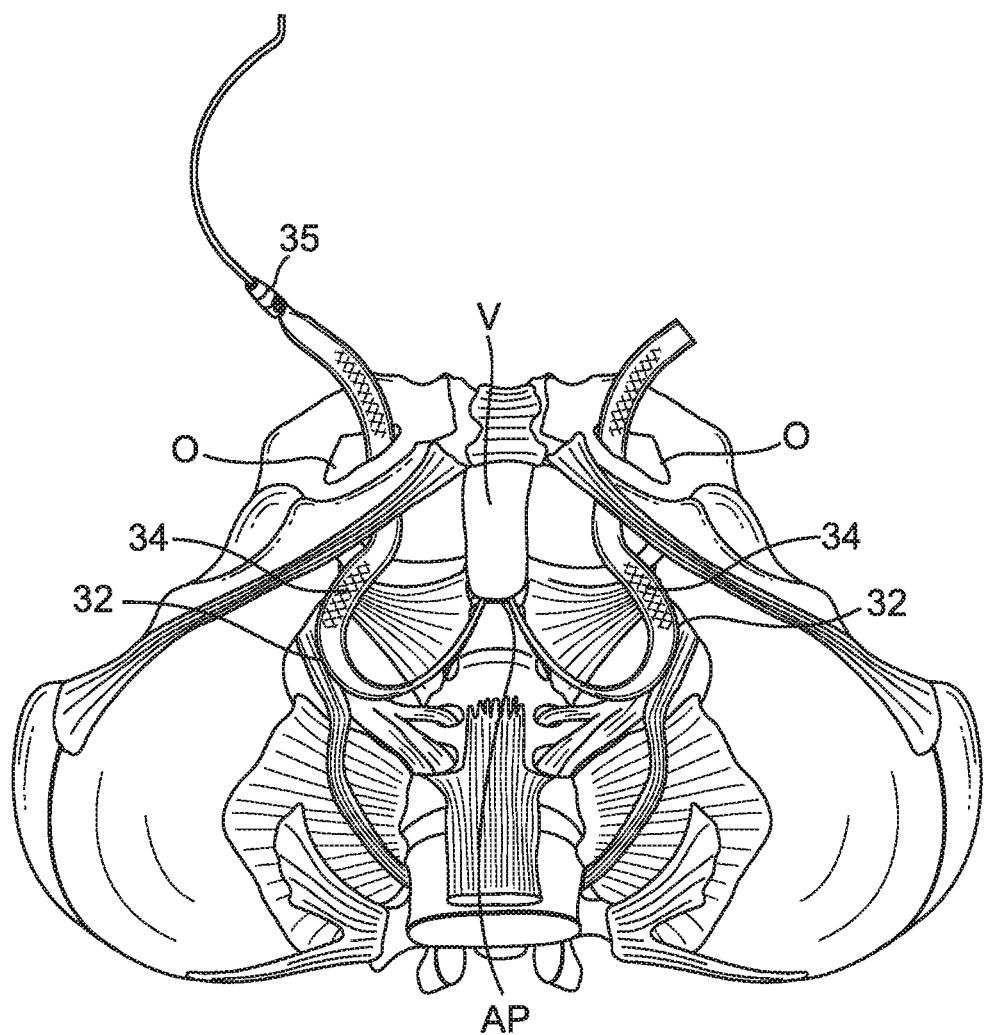
Figure 20:
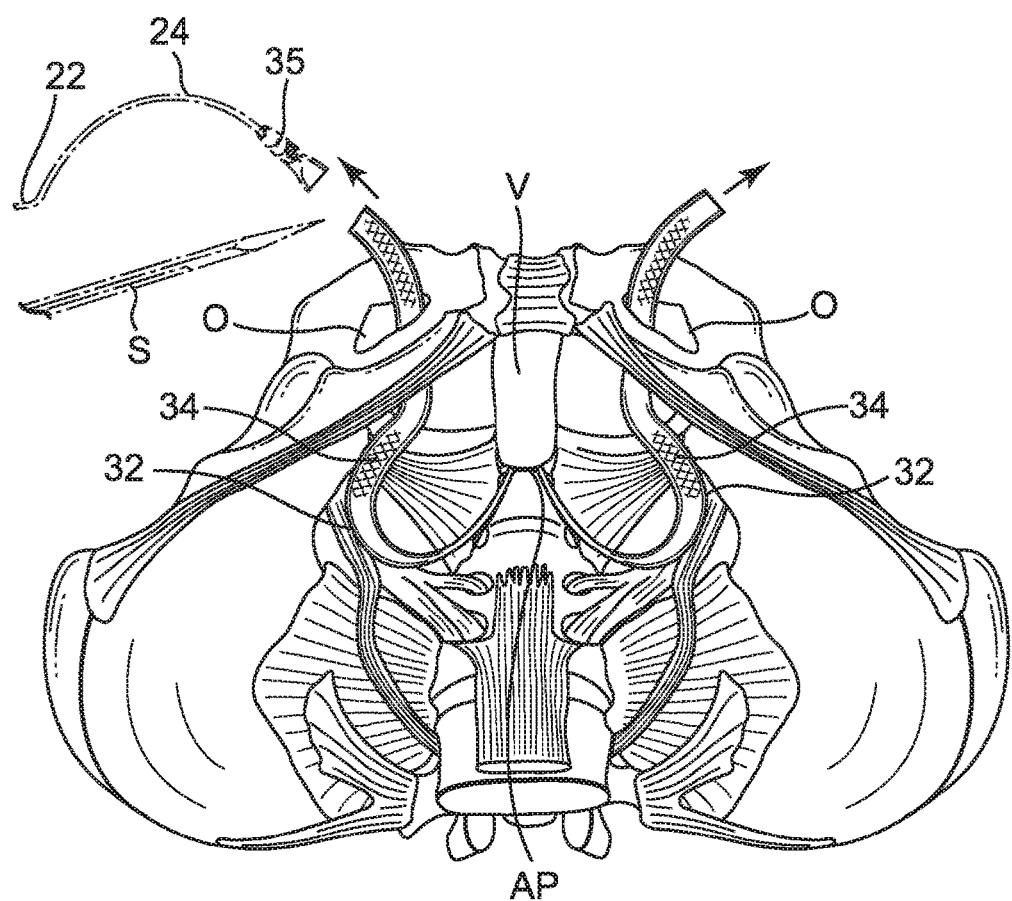

As shown in FIGS. 18, 19 and 20, the same procedure is accomplished on the opposite side of the patient with the opposite end of the implant assembly 30.

Figure 20A:
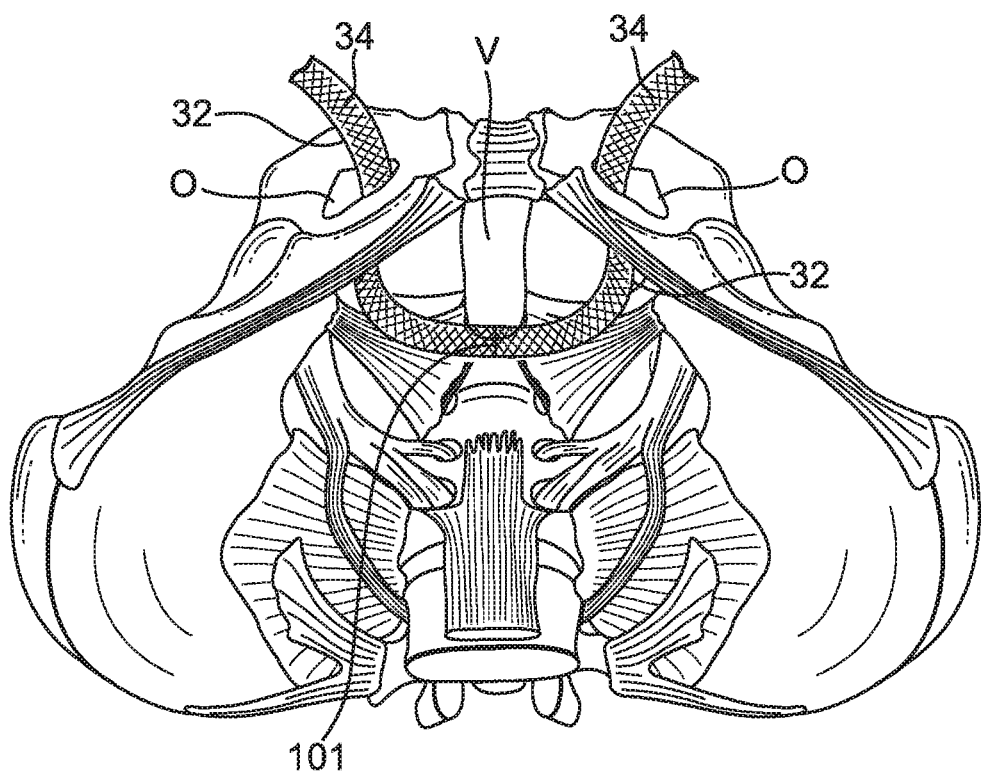
FIG. 20A illustrates the implant attached (e.g. stitched) to the vagina in the region of the apex.

As shown in FIG. 20A, the implant 34 may be fixed to the vaginal wall with two stitches 101 about 1.5 cm from the apex AP. It can also be fixed to the rectum (e.g. in the region or directly to) with two other stitches. The implant 34 is between the vagina and rectum. Its passage through the levator ani is on both sides, the fixation point of the vaginal vault suspension.

Figure 21:
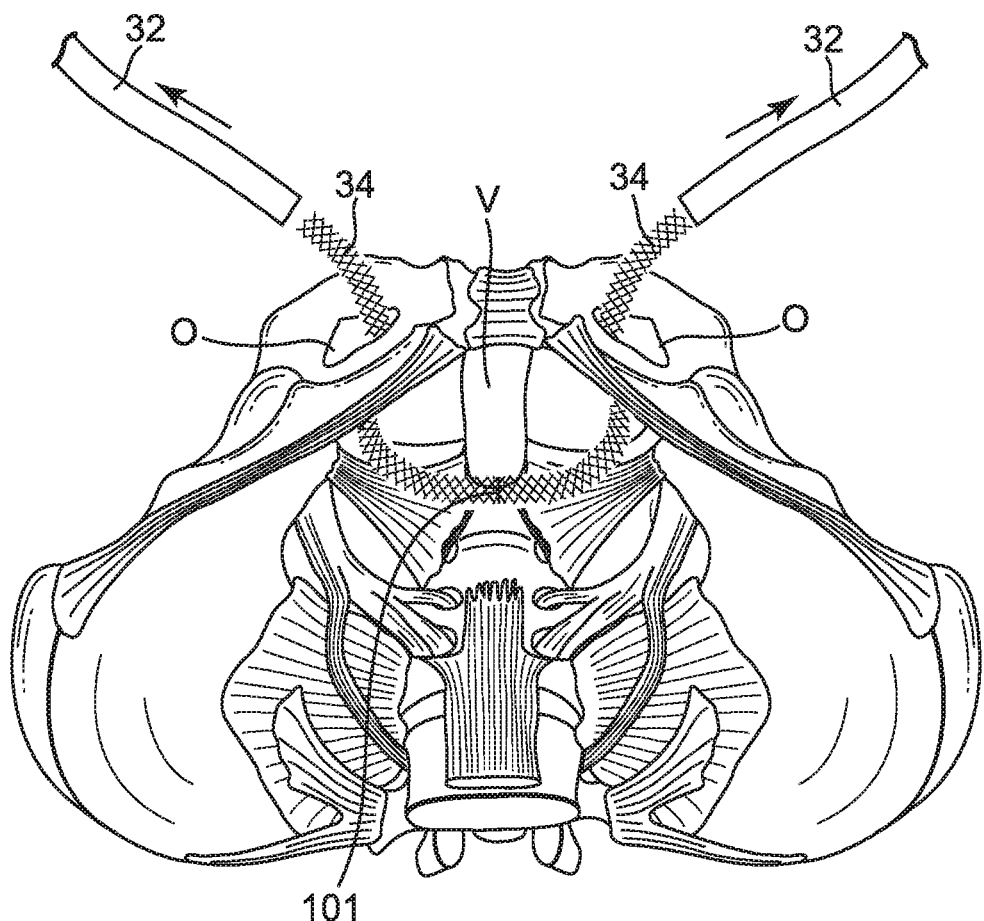
Figure 22:
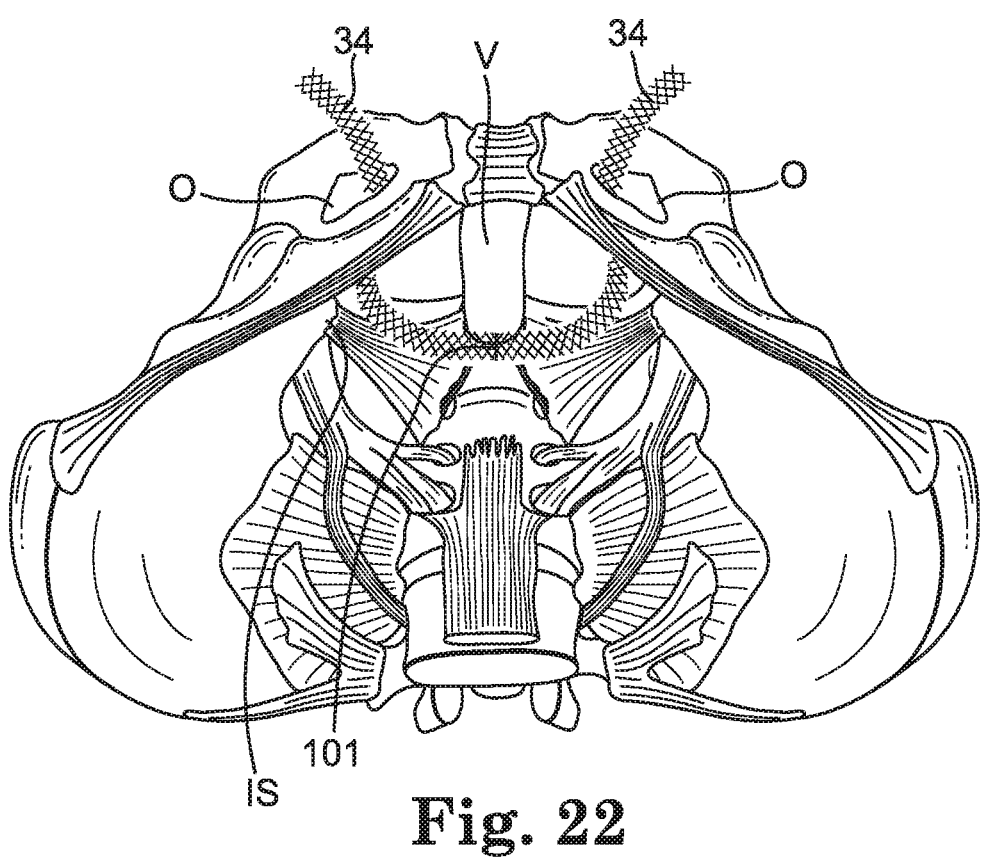

Once the implant 34 is implanted, the insertion sheaths 32 may be removed as shown in FIG. 21. FIG. 22 shows the corrected prolapse with the vagina V supported by implant 34.

The posterior repair can be accomplished with posterior perineo-myorraphy and some times plications of the rectal fascia. The vaginal wall may be closed with a suture from the vaginal apex to the lowest region of the perineum.

Anterior Route Fixation

The stabilization of the vaginal vault can also be accomplished with an anterior route (e.g. if the surgeon prefers this route for surgical reasons). The implant 34 may be implanted by anterior dissection of the anterior vaginal wall. The bladder is dissected off the vagina. The para-vesical space is opened on both sides going to the ischial spines IS.

The needles 10 and 20 may be used similarly in the posterior procedure and the implant can be fit through muscular wall in both sides. The implant 34 may be fixed to the anterior part of the vaginal vault at the apex AP.

All patents, patent applications, journal articles and publications mentioned herein are expressly incorporated by reference in their entirety.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method for treating a pelvic disorder in a patient, comprising:
   providing a first surgical instrument and a second surgical instrument, the first and second surgical instruments including a needle portion, the needle portion having a generally straight portion and a helical portion having a distal end region, wherein the generally straight portion of at least one of the first and second instruments has a longitudinal axis and the helical portion has an axis that is not parallel to the longitudinal axis of the straight portion;
   providing an implant;
   creating a vaginal incision in a vagina;
   passing the distal end region of the first surgical instrument through the vaginal incision;
   associating the implant with the first surgical instrument;
   passing the distal end region of the second surgical instrument through the vaginal incision;
   associating the implant with the second surgical instrument; and
   securing the implant in place to stabilize the vagina.

2. The method of claim 1, wherein creating the vaginal incision includes creating the vaginal incision in a region of an apex of the vagina.

3. The method of claim 1, wherein providing the first and second surgical instruments includes providing at least one of the first and second surgical instruments adapted for right-handed use and the other of the first and second surgical instruments adapted for left-handed use.

4. The method of claim 1, further including attaching the implant to the vagina.

5. The method of claim 1, wherein providing the implant includes providing a mesh implant.

6. The method of claim 5, wherein providing the mesh implant includes providing the mesh implant constructed at least in part of an absorbable material.

7. The method of claim 5, wherein providing the mesh implant includes providing the mesh implant having a separable sleeve.

8. The method of claim 7, wherein the separable sleeve includes at least one dilating connector.

9. The method of claim 8, wherein the at least one dilating connector includes opposing dilating connectors.

10. The method of claim 1, wherein passing the distal end region of the first surgical instrument through the vaginal incision further includes passing the first surgical instrument through an inferior part of an obturator foramen.

11. A surgical method for treating a pelvic disorder in a patient, comprising:
   providing a first surgical instrument including a needle portion, the needle portion having a straight portion and a helical portion having a distal end region, wherein the straight portion of the first instrument has a longitudinal axis and the helical portion has an axis that is not parallel to the longitudinal axis of the straight portion;
   providing a second surgical instrument including a needle portion, the needle portion having a distal end region;
   providing an implant having one or more end dilators;
   passing the distal end region of the first surgical instrument through a vaginal incision, in a vagina, on a first side of the patient;
   associating the implant with the first surgical instrument;
   passing the distal end region of the second surgical instrument through the vaginal incision on a second side of the patient;
   associating the implant with the second surgical instrument; and
   placing the implant to stabilize the vagina.

12. The method of claim 11, wherein providing the implant includes providing the implant constructed at least in part of mesh.

13. The method of claim 11, further including creating the vaginal incision.

14. The method of claim 13, wherein the vaginal incision is in a region of an apex of the vagina.

15. The method of claim 11, wherein the implant includes a separable sleeve.

16. The method of claim 11, further including moving the distal end region of the first surgical instrument or the second surgical instrument through a vaginal incision.

17. The method of claim 11, wherein the first surgical instrument and the second surgical instrument each include a handle portion.

* * * * *